( 12 ) United States Patent
Kunita et al.

(10) Patent No.: US 8,509,029 B2
(45) Date of Patent: Aug. 13, 2013

(54) ULTRASONIC DIAGNOSTIC APPARATUS

(75) Inventors: Masashi Kunita, Kanagawa (JP);
Yasuhiro Nakamura, Kanagawa (JP);
Takashi Sakai, Kanagawa (JP);
Takehiko Suginouchi, Kanagawa (JP)

(73) Assignee: Panasonic Corporation, Osaka (JP)

( * ) Notice: Subject to any disclaimer, the term of this patent is extended or adjusted under 35 U.S.C. 154(b) by 87 days.

(21) Appl. No.: 13/260,161

(22) PCT Filed: Mar. 25, 2010

(86) PCT No.: PCT/JP2010/002133
§ 371 (c)(1),
(2), (4) Date: Sep. 23, 2011

(87) PCT Pub. No.: WO2010/116645
PCT Pub. Date: Oct. 14, 2010

(65) Prior Publication Data
US 2012/0020187 A1   Jan. 26, 2012

(30) Foreign Application Priority Data
Mar. 30, 2009   (JP) .................................. 2009-080781

(51) Int. Cl.
*G01S 15/89* (2006.01)
(52) U.S. Cl.
USPC .......................................................... 367/87
(58) Field of Classification Search
USPC ................................. 367/87, 7, 11
See application file for complete search history.

(56) References Cited

U.S. PATENT DOCUMENTS

| 2004/0236223 | A1 | 11/2004 | Barnes et al. | |
| 2004/0258127 | A1 | 12/2004 | Ramamurthy et al. | |
| 2012/0020187 | A1 * | 1/2012 | Kunita et al. | 367/87 |

FOREIGN PATENT DOCUMENTS

| JP | 5-344970 | 12/1993 |
| JP | 8-299335 | 11/1996 |
| JP | 2001-346798 | 12/2001 |
| JP | 2003-070784 | 3/2003 |
| JP | 2003-325508 | 11/2003 |
| WO | WO 2010116645 A1 * | 10/2010 |

* cited by examiner

*Primary Examiner* — Daniel Pihulic
(74) *Attorney, Agent, or Firm* — Hamre, Schumann, Mueller & Larson, P.C.

(57) ABSTRACT

An ultrasonic diagnostic apparatus includes: a plurality of vibration elements (1) that transmit and receive an ultrasonic beam; a plurality of transmission circuits (2) that are connected to the respective vibration elements and output a transmission driving signal to be used for driving the vibration elements; and a transmission power source (3) that supplies electric power to the transmission circuits. The ultrasonic diagnostic apparatus further includes: a pulse detection unit (21) that detects a transmission signal to be used for generating the transmission driving signal; an electric power measurement unit (20) that detects an amount of electric power supplied to the transmission circuits as a whole; a distribution calculation unit (24) that calculates an amount of electric power distributed into each of the vibration elements based on outputs of the pulse detection unit and the electric power measurement unit; and a power distribution derivation unit (22) that derives electric power having been supplied to each of the plurality of vibration elements based on an output of the distribution calculation unit, wherein the transmission driving signal is controlled based on the power distribution derived in the power distribution derivation unit. With this configuration, it is possible to provide a more compact and highly reliable ultrasonic diagnostic apparatus capable of performing a temperature monitoring that detects local heat generation of the vibration elements based on the actual transmission power by using a circuit with a reduced number of components.

6 Claims, 5 Drawing Sheets

ULTRASONIC DIAGNOSTIC APPARATUS

TECHNICAL FIELD

The present invention relates to an ultrasonic diagnostic apparatus, and in particular relates to a technology for managing transmission powers of vibration elements.

BACKGROUND ART

Generally, an ultrasonic probe has an array vibration element (vibration element group) composed of a plurality of vibration elements. The ultrasonic probe outputs ultrasonic beams from the vibration element group to perform electronic scanning. Examples of the electronic scanning type include an electronic linear scanning and an electronic sector scanning.

High-voltage transmission driving signals are supplied to the vibration element group, which causes ultrasound to be transmitted to each of the vibration elements. The ultrasound transmitted from each of the vibration elements is combined to form an ultrasonic beam. A power loss in an electro-acoustic conversion in the vibration element group is output as heat. In other words, the vibration element group generates heat, which then is conducted to each part of the ultrasonic probe. This heat conduction also increases a surface temperature of an acoustic lens. Since the ultrasonic probe comes into direct contact with a living body; it is very important to manage the temperature of the vibration element group or the ultrasonic probe in terms of safety for protecting a living body from burns and the like (there are statutes, safety standards, etc., for the temperature management of the ultrasonic probe).

Here, in the electronic linear scanning, a temperature distribution in the vibration element group along the arrangement direction of the elements is considered. For example, in a color flow mapping mode in which a two-dimensional color flow image (color doppler mode image) is overlaid and displayed on a two-dimensional monochrome tomographic image (B-mode image), for example, the transmission should be performed once for the B-mode and ten times for the color doppler mode per one beam address (the transmission condition varies depending on modes). Moreover, in many cases, a vibration element region where a color doppler mode image is formed is set at a part of the vibration element group. In this case, temperatures at respective locations in the vibration element group are not the same, i.e., the temperature at an area where the transmission for the color doppler mode and the transmission for the B-mode are performed together is increased further. Therefore, if the temperature of the vibration element group is assumed to be uniform without considering a mode or a region where an ultrasonic image is formed, the temperature will be misunderstood locally.

Among conventional ultrasonic diagnostic apparatuses, as a first ultrasonic diagnostic apparatus, there is one that performs temperature management by monitoring a voltage and a current of a commonly-used transmission power source, i.e., monitoring the total amount of electric power related to the transmission.

Further, as a second ultrasonic diagnostic apparatus, a type is proposed (for example, see Patent Document 1) in which the temperature is obtained by a software calculation considering transmission conditions.

Further, as a third ultrasonic diagnostic apparatus, a type is proposed (for example, see Patent Document 2) in which a plurality of transmission power detection circuits are arranged at positions corresponding to the vibration element group so as to obtain temperature based on the detection results. FIG. 5 is a block diagram showing a partial configuration of the third ultrasonic diagnostic apparatus. The ultrasonic diagnostic apparatus includes a plurality of vibration elements 1 (vibration element group 11) that transmit and receive ultrasound, a plurality of transmission circuits 2 (transmission circuit group 12) that input transmission driving signals to the vibration elements 1, a transmission pulse generation unit 4 that supplies transmission pulses to the transmission circuits 2, and a transmission power source 3 that supplies electric power to the transmission circuits 2. The ultrasonic diagnostic apparatus further includes electric power detection units 40 that detect the amount of electric power from transmission driving signals of the respective transmission circuits 2, and a transmission monitoring unit 23 that detects the temperature of the ultrasonic probe from outputs of the electric power detection units 40.

PRIOR ART DOCUMENTS

Patent Documents

[Patent Document 1] JP 2003-70784A
[Patent Document 2] JP 2003-325508A

DISCLOSURE OF INVENTION

Problem to be Solved by the Invention

However, in the conventional first ultrasonic diagnostic apparatus, since the entire vibration element group is evaluated macroscopically, there is a problem in that it is difficult to detect the above-described local heat generation. Further, in such an ultrasonic diagnostic apparatus, the power is limited uniformly at the time of controlling the transmission power, which sometimes limits the power excessively. This causes a problem in that, while the heat generation can be suppressed, the quality of ultrasound images is decreased due to the decrease in the sensitivity of the ultrasonic signal (signal-to-noise ratio).

Further, in the conventional second ultrasonic diagnostic apparatus, the voltage, the wave number and the transmission interval of the transmission pulse are adjusted finely for corresponding to various condition settings such as resolution priority and sensitivity priority, and the operation sequence is complex. Therefore, the amount of calculation is enormous and the content of the calculation is complex, which increases the possibility of a design error and a bug in the system. Further, since the influence by the heat generation is obtained by calculation, the calculation result may not coincide with the actual behavior of the apparatus. For example, when the actual behavior of the apparatus is different from designed transmission conditions owing to a bug in the system or a failure of the apparatus, it is difficult to detect the heat generation status.

Further, in the conventional third ultrasonic diagnostic apparatus, since the amount of electric power to be supplied to each of hundreds of vibration elements driven independently should be measured with sufficient resolution, the occupied area of the circuit is enlarged, which leads to inhibit the integration and the cost reduction. At the same time, the increased number of components for the circuit increases the incidence of failure of the entire apparatus, which may decrease the reliability.

The present invention solves the above-described conventional problems, and its object is to provide a more compact and highly reliable ultrasonic diagnostic apparatus by performing a temperature monitoring that is capable of detecting local heat generation of the vibration element group based on the actual transmission power and performing the temperature monitoring using a circuit with a reduced number of components.

Means for Solving Problem

An ultrasonic diagnostic apparatus of the present invention includes: a plurality of vibration elements that transmit and receive an ultrasonic beam; a plurality of transmission circuits that are connected to the respective vibration elements and output a transmission driving signal to be used for driving the vibration elements; and a transmission power source that supplies electric power to the transmission circuits. In order to solve the above-described problems, the ultrasonic diagnostic apparatus further includes: a pulse detection unit that detects a transmission signal to be used for generating the transmission driving signal; an electric power measurement unit that detects an amount of electric power supplied to the transmission circuits as a whole; a distribution calculation unit that calculates an amount of electric power distributed into each of the vibration elements based on outputs of the pulse detection unit and the electric power measurement unit; and a power distribution derivation unit that derives electric power having been supplied to each of the plurality of vibration elements based on an output of the distribution calculation unit, wherein the transmission driving signal is controlled based on the power distribution derived in the power distribution derivation unit.

Further, the ultrasonic diagnostic apparatus of the present invention can be configured further to include a transmission pulse generation unit that generates a transmission pulse to be input to each of the plurality of transmission circuits; and a transmission control unit that generates a control signal to be used for controlling the transmission pulse generation unit based on the power distribution, wherein the transmission signal is the transmission pulse.

Further, the ultrasonic diagnostic apparatus of the present invention can be configured to include a transmission pulse generation unit that generates a transmission pulse to be input to each of the plurality of transmission circuits; and a transmission control unit that generates a control signal to be used for controlling the transmission pulse generation unit based on the power distribution, wherein the transmission signal is the control signal.

Further, it is possible to have a configuration in which the pulse detection unit and the electric power measurement unit perform detection and measurement, respectively, per each ultrasonic beam to be transmitted.

Further, it is possible to have a configuration in which the pulse detection unit detects a frequency of a pulse output from the transmission pulse generation unit. In this case, the output from the distribution calculation unit is the power distribution, and the power distribution derivation unit becomes unnecessary.

Further, it is possible to have a configuration in which at least one of the pulse detection unit, the electric power measurement unit and the distribution calculation unit includes a connection selection unit capable of switching processing per mode of each ultrasonic beam to be transmitted.

Further, it is possible to have a configuration in which the transmission power source is composed of a plurality of power sources, and a plurality of the electric power measurement units are provided in such a manner as to correspond to the plurality of power sources.

Effect of the Invention

According to the present invention, it is possible to provide a compact and highly reliable ultrasonic diagnostic apparatus capable of performing a temperature monitoring that detects local heat generation of a vibration element group based on the actual transmission power by derivation of a power distribution, and performing the temperature monitoring using a circuit with a reduced number of components.

DESCRIPTION OF EMBODIMENTS

Hereinafter, embodiments of the ultrasonic diagnostic apparatus of the present invention will be described specifically with reference to the drawings.

Embodiment 1

Figure 1:
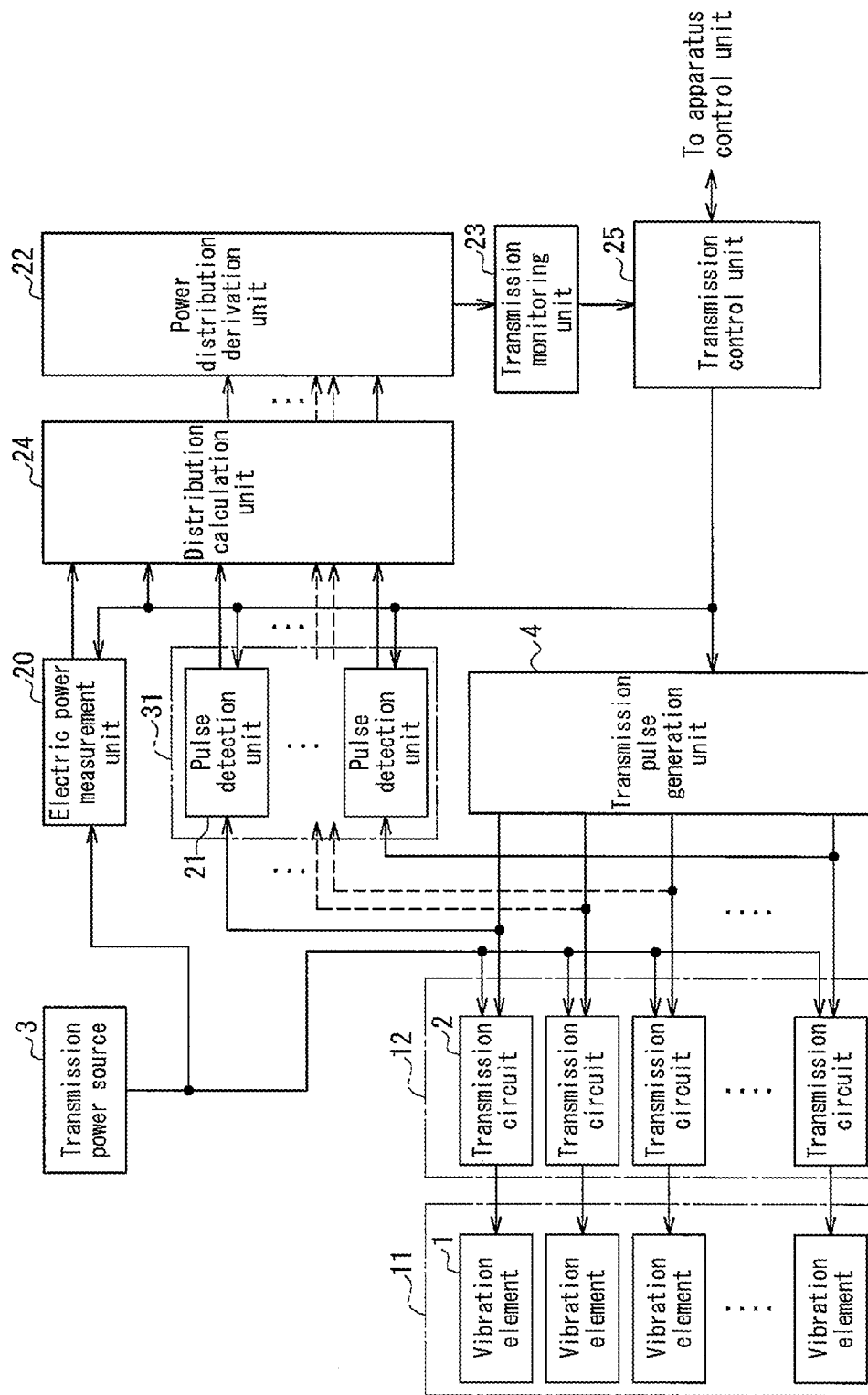
FIG. 1 is a block diagram of an ultrasonic diagnostic apparatus in Embodiment 1 of the present invention.

FIG. 1 is a block diagram showing a configuration of an ultrasonic diagnostic apparatus according to Embodiment 1 of the present invention. A vibration element group 11 is provided in an ultrasonic probe (not shown), and is composed of a plurality of vibration elements 1. The vibration elements 1 are driven by transmission driving signals from corresponding transmission circuits 2, and transmit ultrasound. The ultrasound transmitted by the plurality of vibration elements 1 is overlapped to form an ultrasonic beam. By controlling the transmission driving signal, a subject can be scanned by the ultrasonic beam. For example, by sequentially changing the vibration element to be driven among the plurality of vibration elements 1, an electronic linear scanning can be performed with respect to the subject.

Further, the vibration elements 1 receive ultrasound having been reflected from the subject. The ultrasonic signals received by the vibration elements 1 are processed by a signal processing unit (not shown) so as to be displayed on a display part as ultrasonic images or the like.

A transmission circuit group 12 is composed of a plurality of transmission circuits 2. The transmission circuits 2 output transmission driving signals for driving the corresponding vibration elements 1 (for example, one-to-one correspondence) based on transmission pulses from a transmission pulse generation unit 4 and electric power supplied from a transmission power source 3.

The transmission pulse generation unit 4 outputs transmission pulses having a predetermined delay relationship with one another with respect to each of the transmission circuits 2, based on a signal from a transmission control unit 25. The transmission power source 3 supplies electric power to each of the plurality of transmission circuits 2. The transmission control unit 25 is connected to an apparatus control unit for controlling each unit based on an instruction in a diagnostic mode or the like from an operator, and in particular, for supplying a control signal for instructing the transmission pulse generation unit 4 to switch the diagnostic mode, etc.

In the present embodiment, for monitoring the temperature in the vibration element group 11, an electric power measurement unit 20 as well as a pulse detection unit group 31 that is composed of pulse detection units 21 corresponding to the respective transmission circuits 2 are provided.

The pulse detection unit group 31 is composed of a plurality of pulse detection units 21 that correspond to the transmission circuits 2. The pulse detection units 21 are circuits that detect transmission pulses input from the transmission pulse generation unit 4 to the corresponding transmission circuits 2. Naturally, the type of the transmission pulse can be selected arbitrarily for also detecting other information as long as the information is used for deriving the power distribution derivation. The electric power measurement unit 20 is a circuit that measures an amount of electric power supplied from the transmission power source 3 to the transmission circuit group 12. Specific processings of the pulse detection unit group 31 and the electric power measurement unit 20 will be described in Embodiments 3 and 4.

A distribution calculation unit 24 is connected with the electric power measurement unit 20 and the pulse detection unit group 31 so as to receive an electric power measurement result from the electric power measurement unit 20 and a transmission pulse detection result from the pulse detection unit group 31. Based on the electric power measurement result and the transmission pulse detection result, the distribution calculation unit 24 distributes values of the electric power measurement result into each of the vibration elements 1 in which transmission pulses are detected. A power distribution derivation unit 22 performs accumulation processing, etc., on the values of the electric power measurement result distributed from the distribution calculation unit 24, thereby deriving electric power (power distribution) per the vibration element 1.

Based on the power distribution derived in the power distribution derivation unit 22, for example, a transmission monitoring unit 23 calculates an amount of heat generated per the vibration element 1 for calculating a surface temperature of the ultrasonic probe. When the surface temperature of the ultrasonic probe exceeds a predetermined judgment value, the transmission monitoring unit 23 outputs an alarm signal to the transmission control unit 25. Upon receiving the alarm signal, the transmission control unit 25 performs a control so that the amount of heat generation in the vibration elements 1 is suppressed by reducing the electric power of the transmission driving signal, for example.

Figure 2:
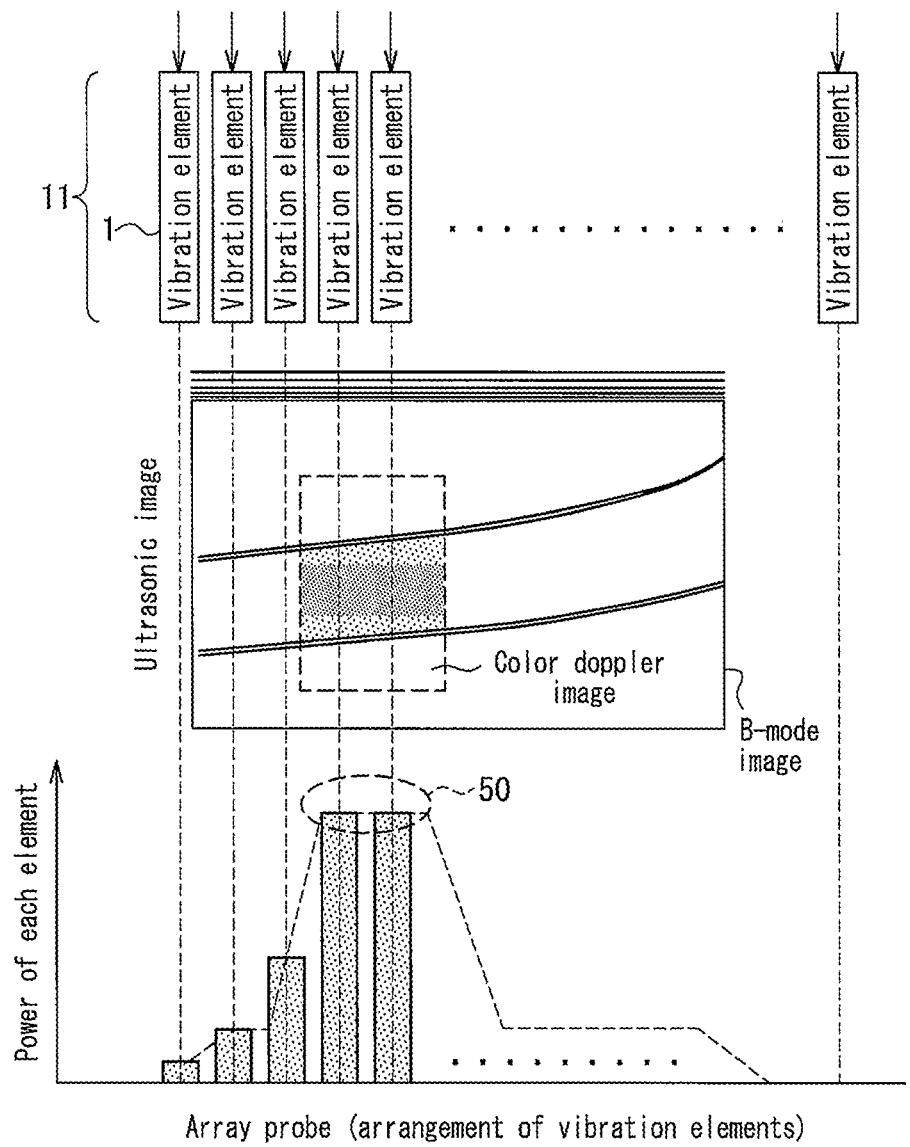
FIG. 2 shows a relationship between an ultrasonic diagnostic image and power of a vibration element group corresponding to the ultrasonic diagnostic image.

FIG. 2 shows an ultrasonic image in which a color doppler mode image is overlaid on a B-mode image and a view in which each of the arranged vibration elements 1 are associated with the amount of electric power (power) supplied to the vibration element 1. In a color flow mapping mode in which a color doppler mode image is overlaid on a B-mode image, since vibration elements for the color doppler mode image also serve as vibration elements for the B-mode image, the power to be supplied to each of the vibration elements 1 varies. In this color flow mapping mode, a large amount of power is supplied to the vibration elements 1 corresponding to a power peak portion 50, which generates a large amount of heat.

In the ultrasonic diagnostic apparatus according to the present embodiment, transmission pulses for the B-mode image and transmission pulses for the color doppler mode image are detected per the vibration element. Therefore, even when the temperature rises locally, it can be detected.

Further, since the power distribution is derived based on the amount of electric power actually supplied from the transmission power source 3 and the transmission pulses actually input to the transmission circuits 2, the temperature status of the vibration element group 11 can be detected even when the actual behavior of the apparatus is different from designed transmission conditions owing to a bug in the system or a failure of the apparatus.

Figure 5:
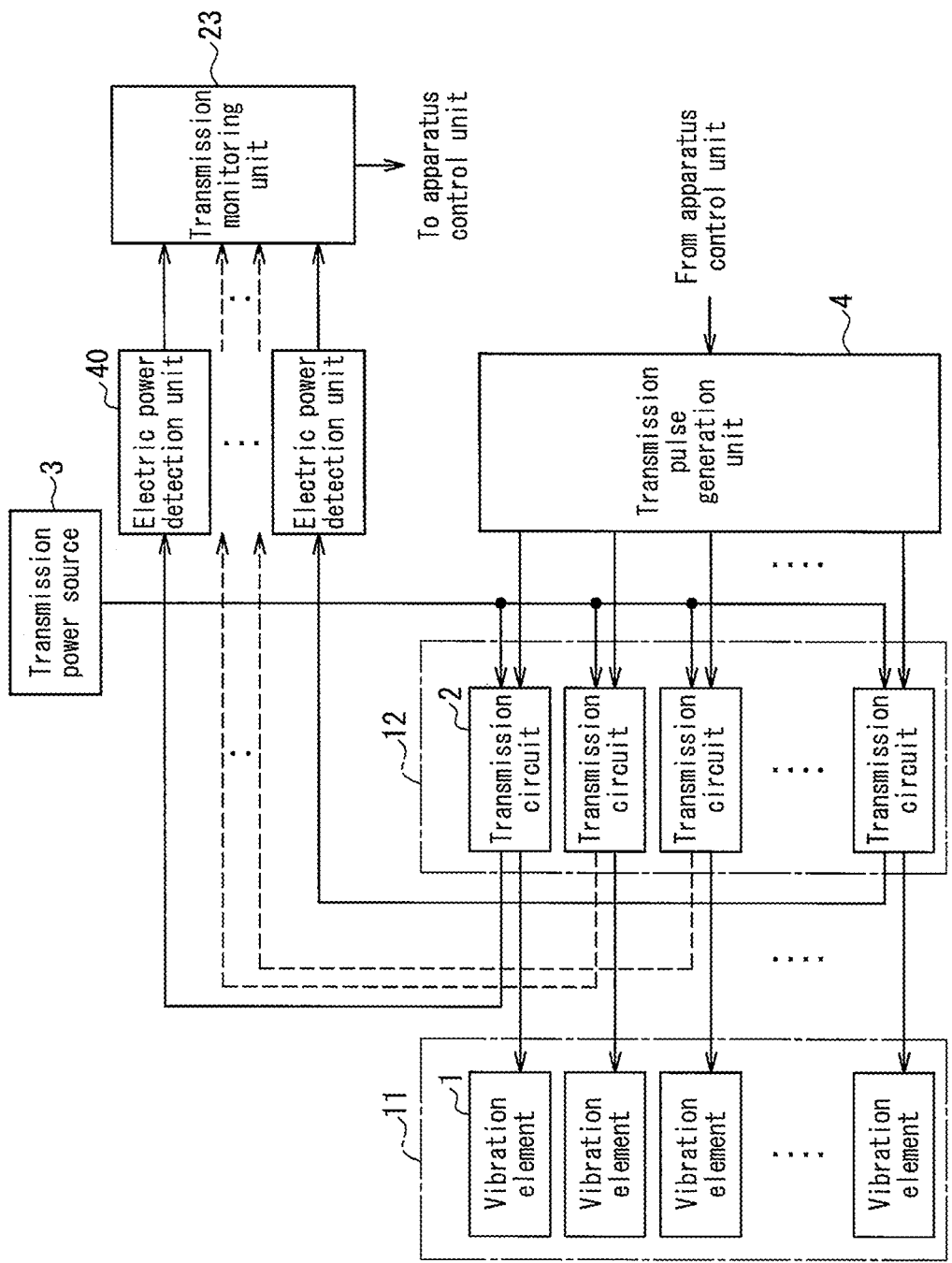
FIG. 5 is a block diagram of a conventional ultrasonic diagnostic apparatus.

Further, unlike electric power detection units 40 of a conventional ultrasonic diagnostic apparatus such as that shown in FIG. 5 that measure the amount of electric power (physical quantity) supplied to the transmission circuits 2, the pulse detection units 21 are configured to detect a transmission pulse, which is a signal for providing timing. Therefore, for example, it is unnecessary to provide circuits such as an A/D converter in the pulse detection units 21, which makes it possible to downsize the pulse detection unit group 31.

As described above, the ultrasonic diagnostic apparatus according to the present embodiment includes the electric power measurement unit 20 that measures electric power supplied from the transmission power source 3, the pulse detection unit group 31 that detects transmission pulses supplied to each of the transmission circuits 2, the distribution calculation unit 24, the power distribution derivation unit 22 and the transmission monitoring unit 23. With this configuration, even when the local heat generation or local temperature rise occurs in the vibration element group or on the ultrasonic probe surface, it is possible to calculate the temperature.

Further, since the power distribution is derived based on the amount of electric power actually supplied and the transmission pulses actually generated, the heat generation and the temperature status of the vibration element group 11 can be calculated even when the actual behavior of the apparatus is different from the designed transmission conditions. Therefore, the subject can be diagnosed safely.

Further, as compared with the case of the conventional technology shown in FIG. 5 in which a plurality of electric power detection units 40 are provided, the pulse detection unit group 31 can be configured to be smaller using a circuit with the reduced number of components, whereby the ultrasonic diagnostic apparatus according to the present embodiment is compact and highly reliable yet with lower cost.

Note here that the transmission pulse output from the transmission pulse generation unit 4 may be any transmission pulse because it is a signal for providing timing, and examples thereof include pulses of various waves, such as a rectangular wave, a sine wave, a burst wave or a chirp wave.

Further, the present embodiment explains the case in which the transmission monitoring unit 23 and the transmission control unit 25 calculate the heat generation and the temperature of the vibration element group 11, and perform a control so that the transmission power is suppressed when the temperature exceeds a predetermined judgment value. However, the present embodiment is not limited to this case. For example, by calculating the surface temperature of the ultrasonic probe and increasing the transmission power until the temperature reaches the predetermined judgment value, the sensitivity of the ultrasonic signal (signal-to-noise ratio) can be improved further, thereby obtaining the ultrasonic diagnostic apparatus having a higher image quality.

Embodiment 2

The constituent elements of an ultrasonic diagnostic apparatus according to Embodiment 2 of the present invention are identical to the constituent elements of the ultrasonic diagnostic apparatus according to Embodiment 1. Therefore, the same constituent elements are denoted with the same reference numerals as those of the ultrasonic diagnostic apparatus according to Embodiment 1, and the explanation thereof is omitted. Hereinafter, the ultrasonic diagnostic apparatus according to the present embodiment will be described with reference to the block diagram of FIG. 1.

In the present embodiment, the pulse detection unit group 31 is integrated on the same IC as the transmission pulse generation unit 4 and the power distribution derivation unit 22. Since the pulse detection unit group 31 detects the transmission pulse that is a signal for indicating the timing of the transmission driving signal, it is unnecessary to provide circuits such as an A/D converter. Therefore, the pulse detection unit group 31 can be integrated on an IC easily.

Here, by integrating the pulse detection unit group 31 composed of the pulse detection units 21 that correspond to several hundreds of the vibration elements 1 on an IC, the circuit can be configured smaller at low cost. Further, by mounting the pulse detection unit group 31 together on the IC on which the transmission pulse generation unit 4 and the power distribution derivation unit 22 are placed, it is possible to reduce further the number of components to be mounted on the substrate. Thus, the incidence of failure of the entire ultrasonic diagnostic apparatus can be reduced, and thus the reliability of the product can be improved.

As described above, in the ultrasonic diagnostic apparatus according to the present embodiment, by integrating the pulse detection unit group 31 on the IC, the pulse detection unit group 31 can be made small at low cost and the number of components can be reduced. Therefore, it is possible to obtain a compact, highly reliable and safe yet low-cost ultrasonic diagnostic apparatus.

Note here that the pulse detection units 21 can be configured so as to correspond selectively to a part of the vibration elements, instead of corresponding to all of the vibration elements 1. With this configuration, the circuit scale of the pulse detection unit group 31, the distribution calculation unit 24 and the power distribution derivation unit 22 can be downsized further, whereby it is possible to obtain a compact yet lower cost ultrasonic diagnostic apparatus.

Embodiment 3

The constituent elements of an ultrasonic diagnostic apparatus according to Embodiment 3 of the present invention are identical to the constituent elements of the ultrasonic diagnostic apparatus according to Embodiment 1. Therefore, the same constituent elements are denoted with the same reference numerals as those of the ultrasonic diagnostic apparatus according to Embodiment 1, and the explanation thereof is omitted. Hereinafter, the ultrasonic diagnostic apparatus according to the present embodiment will be described with reference to the block diagram of FIG. 1.

The pulse detection units 21 detect the presence/absence of transmission pulses per the transmission of the ultrasonic beam. The electric power measurement unit 20 measures the amount of electric power supplied from the transmission power source 3 to the transmission circuit group 12 per the transmission of the ultrasonic beam. The distribution calculation unit 24 distributes the measured value of the amount of electric power into each of the vibration elements 1 per the transmission of the ultrasonic beam.

With the above-described configuration, a power distribution corresponding to the vibration element group 11 can be derived per the transmission, whereby the temperature can be estimated more accurately even in a complex diagnostic mode.

Next, the operation in the color flow mapping mode will be described with reference to FIG. 2. First, the electric power measurement unit 20 measures the amount of electric power supplied to the transmission circuit group 12 during a period from the start of the transmission for the B-mode image to the end thereof. Further, the pulse detection units 21 detect the presence/absence of transmission pulses supplied to each transmission circuit 2 for the transmission for the B-mode image. Next, based on the amount of electric power measured and the presence/absence of transmission pulses detected, the distribution calculation unit 24 distributes the value of the amount of electric power for the B-mode image into each of the vibration elements 1 that corresponds to the transmission circuit 2 in which transmission pulses are detected. When the transmission for the B-mode image is completed, the distribution calculation unit 24 outputs the calculation result to the power distribution derivation unit 22.

Next, the electric power measurement unit 20 measures the amount of electric power supplied to the transmission circuit group 12 during a period from the start of the transmission for the color doppler mode image to the end thereof. Further, the pulse detection units 21 detect the presence/absence of transmission pulses supplied to each transmission circuit 2 for the transmission for the color doppler mode image. Next, based on the amount of electric power measured and the presence/absence of transmission pulses detected, the distribution calculation unit 24 distributes the value of the amount of electric power for the color doppler mode image into each of the vibration elements 1 corresponding to the transmission circuits 2 in which transmission pulses are detected. When the transmission for the color doppler mode image is completed, the distribution calculation unit 24 outputs the calculation result to the power distribution derivation unit 22.

The power distribution derivation unit 22 derives a power distribution by accumulating the calculation result (physical quantity) of the distribution calculation unit 24 in accordance with transmission characteristics of each ultrasonic beam, and outputs the power distribution to the transmission monitoring unit 23. At this time, characteristics of heat generated by the transmission of the ultrasonic beam vary depending on modes. Although the transmission for the color doppler mode image sometimes generates more heat than the transmission for the B-mode image, effects by respective transmissions having different heat generation characteristics can be calculated more accurately by performing the measurement, detection and calculation per transmission.

As described above, in the ultrasonic diagnostic apparatus according to the present embodiment, the electric power measurement unit 20, the pulse detection units 21 and the distribution calculation unit 24 respectively perform the measurement, detection and calculation per the transmission of the ultrasonic beam. With this configuration, effects by the transmission of the ultrasonic beam in respective modes having different heat generation characteristics can be calculated more accurately. Thus, it is possible to provide a safer ultrasonic diagnostic apparatus.

Embodiment 4

The constituent elements of an ultrasonic diagnostic apparatus according to Embodiment 4 of the present invention are identical to the constituent elements of the ultrasonic diagnostic apparatus according to Embodiment 3. Therefore, the same constituent elements are denoted with the same reference numerals as those of the ultrasonic diagnostic apparatus according to Embodiment 3, and the explanation thereof is omitted. Hereinafter, the ultrasonic diagnostic apparatus according to Embodiment 4 will be described with reference to the block diagram of FIG. 1.

The ultrasonic diagnostic apparatus according to Embodiment 3 measures the amount of electric power supplied to the transmission circuit group 12, detects the presence/absence of transmission pulses, and calculates the power distribution per the transmission of the ultrasonic beam. The ultrasonic diagnostic apparatus according to the present embodiment measures the amount of electric power supplied to the transmission circuit group 12, detects the number (frequency) of transmission pulses, and calculates the power distribution in a predetermined unit of time. With this configuration, the power distribution derivation unit 22 becomes unnecessary.

The electric power measurement unit 20 measures the amount of electric power from the transmission power source 3 to the transmission circuit group 12 in the unit of time. The pulse detection units 21 have a counter for detecting the number of transmission pulses in the unit of time. The distribution calculation unit 24 distributes the value of the amount of electric power measured in the unit of time into each of the vibration elements 1 based on the amount of electric power and the number of transmission pulses. The value of the amount of electric power distributed is a power distribution per the unit of time, which then is output to the transmission monitoring unit 23.

Since the power distribution derivation unit 22 according to Embodiment 3 requires a circuit for accumulating power (physical quantity) with sufficient resolution, an adequate circuit scale is required correspondingly. In the present embodiment, by detecting the frequency of the transmission pulses in the pulse detection units 21, the power distribution derivation unit 22 having a circuit for accumulating physical quantities becomes unnecessary.

As described above, the ultrasonic diagnostic apparatus according to the present embodiment measures the amount of electric power supplied to the transmission circuit group 12, detects the number of transmission pulses, and calculates the power distribution in a predetermined unit of time. Therefore, the power distribution derivation unit 22 having an accumulation circuit becomes unnecessary, which makes it possible to reduce the total size of the circuit related to the power distribution derivation (the electric power measurement unit 20, pulse detection unit group 31 and distribution calculation unit 24). Thus, it is possible to provide a compact yet low-cost ultrasonic diagnostic apparatus.

Embodiment 5

The constituent elements of an ultrasonic diagnostic apparatus according to Embodiment 5 of the present invention are identical to the constituent elements of the ultrasonic diagnostic apparatus according to Embodiment 1. Therefore, the same constituent elements are denoted with the same reference numerals as those of the ultrasonic diagnostic apparatus according to Embodiment 1, and the explanation thereof is omitted. The ultrasonic diagnostic apparatus according to the present embodiment is characterized by the electric power measurement unit 20. Hereinafter, this characteristic part will be described with reference to FIGS. 1 and 3.

Figure 3:
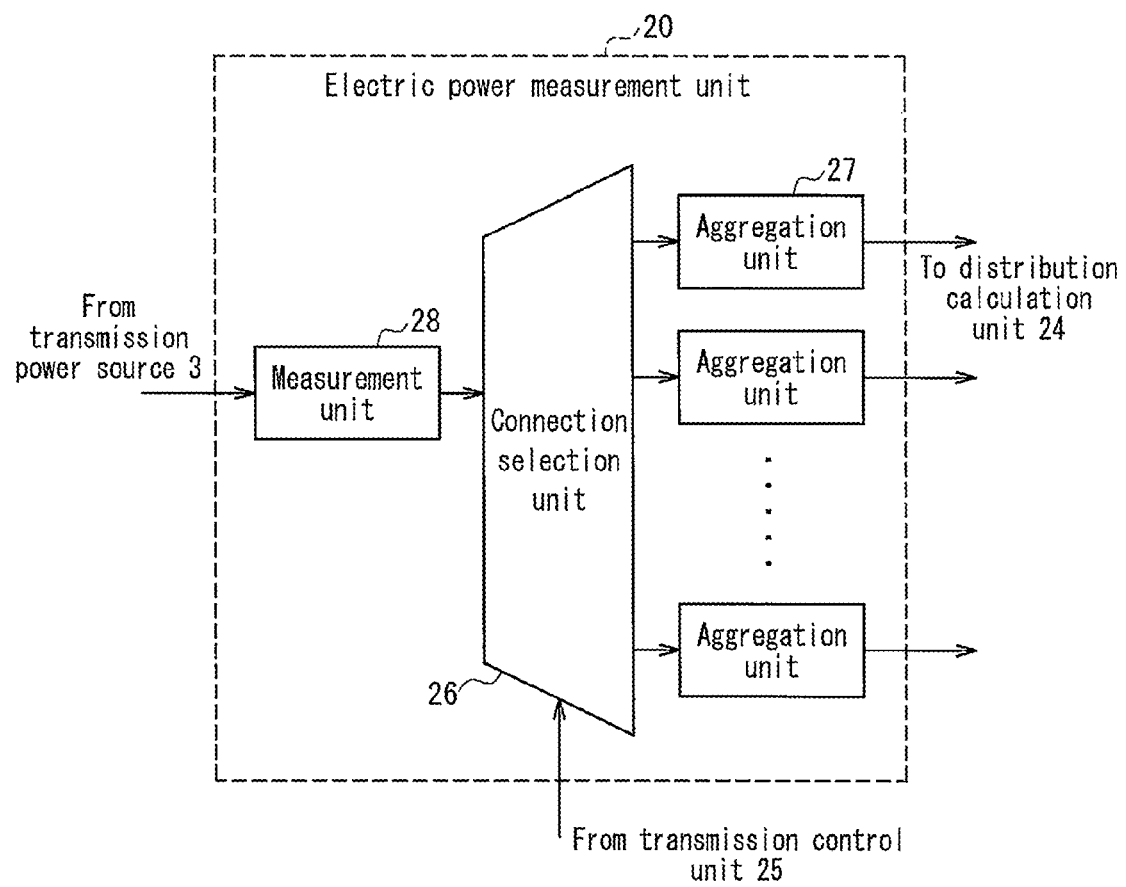
FIG. 3 is a block diagram of an electric power measurement unit of an ultrasonic diagnostic apparatus in Embodiment 5 of the present invention.

FIG. 3 is a block diagram showing a configuration of the electric power measurement unit 20 of the ultrasonic diagnostic apparatus according to the present embodiment. The electric power measurement unit 20 includes a measurement unit 28, a connection selection unit 26 and a plurality of aggregation units 27. The measurement unit 28 measures the amount of electric power supplied from the transmission power source 3 to the transmission circuit group 12. The connection selection unit 26 changes an aggregation unit 27 to be connected with the measurement unit 28 based on the instruction from the transmission control unit 25, so as to convey the amount of electric power measured by the measurement unit 28 to the aggregation unit 27. By this connection change, when ultrasonic images are generated using a plurality of modes for example, measurement results of the amount of electric power can be classified and output according to the type of the transmission pulse and the diagnostic mode by changing the connection per mode. Each aggregation unit 27 aggregates the amount of electric power conveyed in a predetermined time, and outputs it to the distribution calculation unit 24.

Next, the operation in the color flow mapping mode of the ultrasonic diagnostic apparatus according to the present embodiment will be described with reference to FIG. 2. First, the transmission control unit 25 instructs the transmission pulse generation unit 4 and the connection selection unit 26 of the electric power measurement unit 20 that the transmission for the B-mode image is performed. Based on the instruction from the transmission control unit 25, the connection selection unit 26 connects the measurement unit 28 to an appropriate aggregation unit 27. Next, based on the instruction from the transmission control unit 25, the transmission pulse generation unit 4 generates transmission pulses, which then are input to the respective transmission circuits 2 and counted at the respective pulse detection units 21.

The transmission circuits 2 generate transmission driving signals based on the transmission pulses and the electric power supplied from the transmission power source 3. The vibration elements 1 emit ultrasound by being driven by the transmission driving signals, and receive ultrasound having been reflected from the subject. The signals received by the vibration elements 1 are converted into B-mode image data at a circuit processing unit (not shown).

In the electric power measurement unit 20, the measurement unit 28 detects the amount of electric power supplied to the transmission circuit group 12 in the transmission for the B-mode image. The amount of electric power detected is aggregated at the aggregation unit 27 that is connected to the connection selection unit 26.

Next, the transmission control unit 25 instructs the transmission pulse generation unit 4 and the connection selection unit 26 of the electric power measurement unit 20 that the transmission for the color doppler mode image is performed. Based on the instruction from the transmission control unit 25, the connection selection unit 26 changes the connection of the measurement unit 28 to an appropriate aggregation unit 27. Next, based on the instruction from the transmission control unit 25, the transmission pulse generation unit 4 generates transmission pulses, which then are supplied to the respective transmission circuits 2 and counted at the respective pulse detection units 21.

The transmission circuits 2 generate transmission driving signals based on the transmission pulses and the electric power supplied from the transmission power source 3. The vibration elements 1 emit ultrasound by being driven by the transmission driving signals, and receive ultrasound having been reflected from the subject. The signals received by the vibration elements 1 are converted into color doppler mode image data at the circuit processing unit (not shown).

In the electric power measurement unit 20, the measurement unit 28 detects the amount of electric power supplied to the transmission circuit group 12 in the transmission for the color doppler mode image. The amount of electric power detected is aggregated at the aggregation unit 27 that is connected to the connection selection unit 26.

Next, the distribution calculation unit 24 assigns weights to outputs from each aggregation unit 27. Then, the power distribution derivation unit 22 derives a power distribution per the vibration element 1 based on the amounts of electric power supplied to the respective vibration elements 1 that are output from the distribution calculation unit 24. Hereinafter, the temperature of the ultrasonic probe is calculated in the same procedure as Embodiment 1.

As described above, in the present embodiment, since the electric power measurement unit 20 includes the measurement unit 28, the connection selection unit 26 and the plurality of aggregation units 27 in the inside, a contribution due to a temperature rise per mode can be calculated with respect to a plurality of diagnostic modes, which makes it possible to calculate the surface temperature of the ultrasonic probe accurately. Therefore, it is possible to provide a safer ultrasonic diagnostic apparatus.

Note here that, as shown in FIG. 3, the present embodiment explains the case in which the electric power measurement unit 20 is provided with a mechanism of calculating the amount of electric power per mode. However, the present embodiment is not limited to this case. For example, also in a case in which the pulse detection unit group 31 is provided with the same configuration as that shown in FIG. 3, it is possible to calculate the surface temperature of the ultrasonic probe more accurately even in a complex diagnostic mode.

Embodiment 6

The constituent elements of an ultrasonic diagnostic apparatus according to Embodiment 6 of the present invention are identical to the constituent elements of the ultrasonic diagnostic apparatus according to Embodiment 1, except that pluralities of the transmission power sources 3 and the electric power measurement units 20 are formed and the distribution calculation unit 24 can process a plurality of values of the amount of electric power measured by the plurality of electric power measurement units 20. In the ultrasonic diagnostic apparatus according to the present embodiment, the same constituent elements as those of the ultrasonic diagnostic apparatus according to Embodiment 1 are denoted with the same reference numerals as those of the ultrasonic diagnostic apparatus according to Embodiment 1, and the explanation thereof is omitted.

Figure 4:
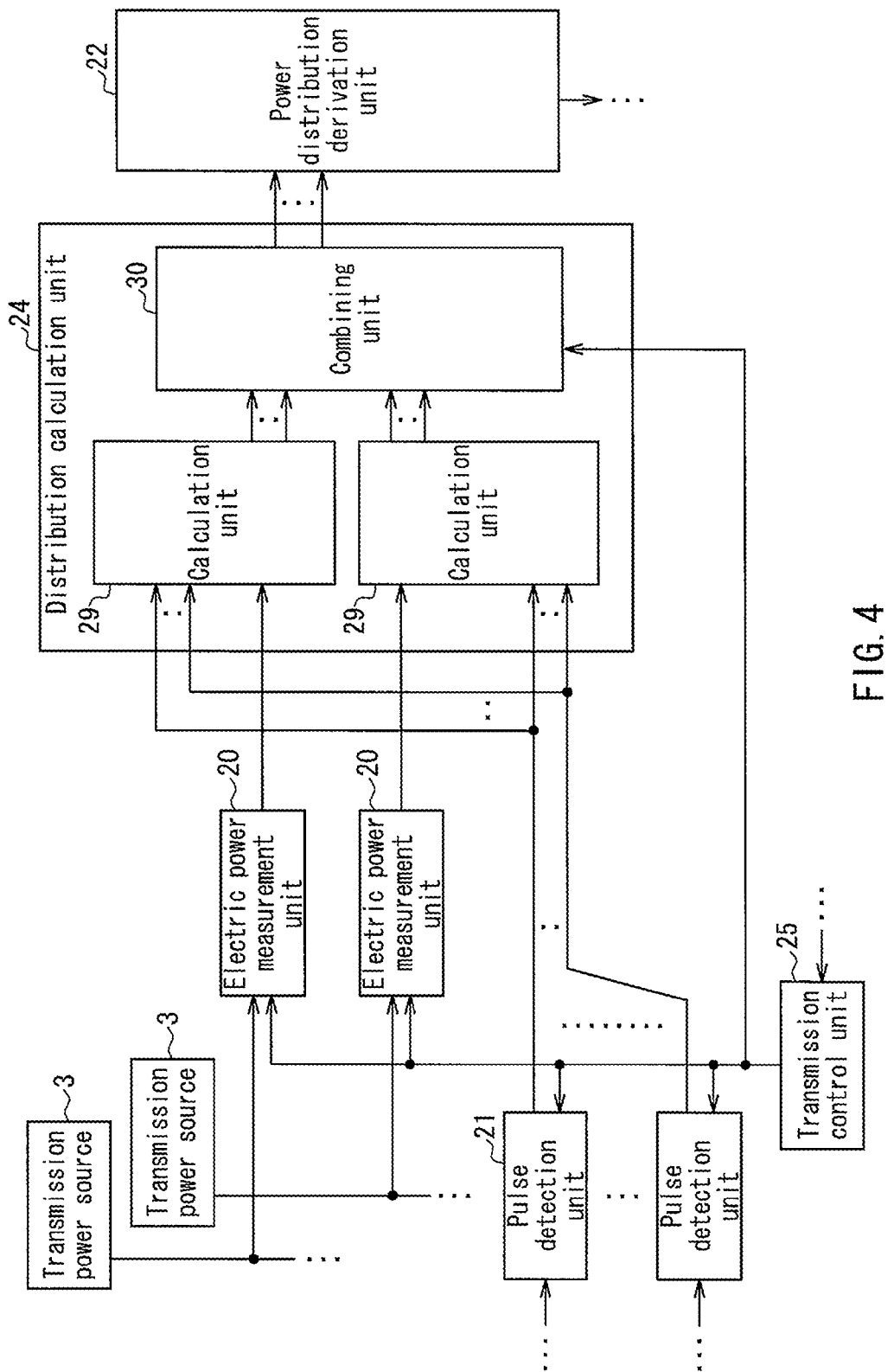
FIG. 4 is a partial block diagram of an ultrasonic diagnostic apparatus in Embodiment 6 of the present invention.

FIG. 4 is a partial block diagram showing a configuration of the ultrasonic diagnostic apparatus according to the present embodiment. A plurality of transmission power sources 3 are provided. For example, in the color flow mapping mode in which a color doppler mode image is overlaid on a B-mode image, the plurality of the transmission power sources 3 are used as independent power sources with respect to the transmission beam for the B-mode image and the transmission beam for the color doppler mode image. With this configuration, the transmission voltages optimum for the respective modes are supplied to the transmission circuit group 12, whereby the quality of the ultrasonic image can be improved and the diagnostic performance can be enhanced.

A plurality of electric power measurement units are provided in such a manner as to correspond to the respective transmission power sources 3. The distribution calculation unit 24 includes a plurality of calculation units 29 provided in such a manner as to correspond to the respective electric power measurement units 20 and a combining unit 30 that combines outputs of the plurality of calculation units 29. The calculation units 29 distribute the value of the amount of electric power into each of the vibration elements 1 based on the amount of electric power detected by the electric power measurement unit 20 and the number of pulses detected by the pulse detection unit 21 in each mode. Further, the calculation units 29 assign predetermined weights to the distributed values of the amount of electric power per mode. For example, the above-described transmission beam for the B-mode image and the above-described transmission beam for the color doppler mode image do not always have the same contribution due to the temperature rise with respect to the amount of power consumption. Such a difference in the contribution is corrected by assigning predetermined weights. The combining unit 30 combines the distributed values of the amount of electric power in each mode and inputs it to the power distribution derivation unit 22.

As described above, in the present embodiment, since the plurality of calculation units 29 corresponding to the plurality of electric power measurement units 20 assign weights to the calculated distributed values of the amount of electric power and the combining unit 30 combines the values, it becomes possible to accurately calculate influences of the temperature rise by the plurality of transmission power sources 3 having different electric voltages. Therefore, the temperature can be calculated more accurately even in a complex diagnostic mode.

Embodiment 7

The constituent elements of an ultrasonic diagnostic apparatus according to Embodiment 7 of the present invention are identical to the constituent elements of the ultrasonic diagnostic apparatus according to Embodiment 1. Therefore, the same constituent elements are denoted with the same reference numerals as those of the ultrasonic diagnostic apparatus according to Embodiment 1, and the explanation thereof is omitted. Hereinafter, the ultrasonic diagnostic apparatus according to the present embodiment will be described with reference to the block diagram of FIG. 1.

The ultrasonic diagnostic apparatus according to Embodiment 1 is configured so that the pulse detection unit group 31 detects the number of pulses using transmission pulses output from the transmission pulse generation unit 4, whereas, the ultrasonic diagnostic apparatus according to the present embodiment is characterized in that the pulse detection unit group 31 detects the number of pulses by detecting control signals from the transmission control unit 25.

The transmission control unit 25 is connected to the transmission pulse generation unit 4 and the pulse detection unit group 31. The transmission control unit 25 inputs control signals to the transmission pulse generation unit 4 and the pulse detection unit group 31. The pulse detection units 21 calculate the number of transmission pulses supplied to the respective transmission circuits 2 from the transmission pulse generation unit 4.

The control signals to be input from the transmission control unit 25 to the respective pulse detection units 21 are the same. One signal line is provided between the transmission control unit 25 and the pulse detection unit group 31, and is branched in the pulse detection unit group 31 to be connected to each of the pulse detection units 21. Alternatively, the pulse detection unit group 31 can be configured as one detection circuit having the same number of outputs as the transmission circuits 2.

As described above, the ultrasonic diagnostic apparatus according to the present embodiment is configured so that each of the pulse detection units 21 operates based on the common control signals output from the transmission control unit 25. With this configuration, the ultrasonic diagnostic apparatus according to the present embodiment can have functions that are equivalent to the ultrasonic diagnostic apparatus according to Embodiment 1 without providing transmission paths for connecting hundreds of the transmission circuits 2 with the pulse detection units 21 one to one. Further, since the number of transmission paths can be reduced, the ultrasonic diagnostic apparatus can be downsized. Therefore, it is possible to provide a compact, highly reliable and safe, yet low-cost ultrasonic diagnostic apparatus.

Embodiment 8

The constituent elements of an ultrasonic diagnostic apparatus according to Embodiment 8 of the present invention are identical to the constituent elements of the ultrasonic diagnostic apparatus according to Embodiment 1. Therefore, the same constituent elements are denoted with the same reference numerals as those of the ultrasonic diagnostic apparatus according to Embodiment 1, and the explanation thereof is omitted. Hereinafter, the ultrasonic diagnostic apparatus according to the present embodiment will be described with reference to the block diagram of FIG. 1.

The ultrasonic diagnostic apparatus according to Embodiment 1 monitors the temperature distribution of the vibration element group 11, whereas the ultrasonic diagnostic apparatus according to the present embodiment monitors a sound output of the vibration element group 11.

Based on the measurement result of the electric power measurement unit 20 and the detection result of the pulse detection unit group 31, the distribution calculation unit 24 calculates the amounts of electric power corresponding to the vibration elements 1 driven by one transmission beam. The power distribution derivation unit 22 derives the power distribution per one transmission beam in a form of an intensity distribution of the sound output. The transmission monitoring unit 23 generates an alarm signal when the intensity of the sound output exceeds a predetermined judgment value. The transmission control unit 25 supplies a control signal to the transmission pulse generation unit 4 so that the intensity of the sound output is controlled based on the alarm signal.

Here, the value of the amount of electric power distributed into each of the vibration elements 1 to be input to the power distribution derivation unit 22 is a value based on the actual transmission power. Therefore, even when the actual behavior of the apparatus is different from the designed transmission conditions owing to a bug in the system or a failure of the apparatus, it is possible to detect the sound output status of the vibration element group 11.

Further, the intensity distribution of the sound output to be output from the power distribution derivation unit 22 is associated with the arrangement of the vibration element group 11. Therefore, even when the output is concentrated locally in a part of the vibration element group 11, it is possible to detect such a local output concentration.

As described above, the present embodiment is configured so that the transmission monitoring unit 23 performs a monitoring using the sound output from the vibration element group 11 as an index. With this configuration, the sound output status associated with the arrangement of the vibration element group 11 can be detected even when the actual behavior of the apparatus is different from the designed transmission conditions. Thus, even when the output is concentrated locally in a part of the ultrasonic probe, the sound output status can be detected. Therefore, as in Embodiment 1, it is possible to provide an ultrasonic diagnostic apparatus that is compact, highly reliable and safe, yet low-cost.

INDUSTRIAL APPLICABILITY

The ultrasonic diagnostic apparatus according to the present invention is capable of performing a temperature monitoring or a sound output monitoring that detects local heat generation of array vibration elements, and is applicable as a safe, highly reliable and compact ultrasonic diagnostic apparatus.

DESCRIPTION OF REFERENCE NUMERALS

1 vibration element
2 transmission circuit
3 transmission power source
4 transmission pulse generation unit
11 vibration element group
12 transmission circuit group
20 electric power measurement unit
21 pulse detection unit
22 power distribution derivation unit
23 transmission monitoring unit
24 distribution calculation unit
25 transmission control unit
26 connection selection unit
27 aggregation unit
28 measurement unit
29 calculation unit
30 combining unit
31 pulse detection unit group
40 electric power detection unit
50 power peak portion of a vibration element group

The invention claimed is:

1. An ultrasonic diagnostic apparatus, comprising:
a plurality of vibration elements that transmit and receive an ultrasonic beam;
a plurality of transmission circuits that are connected to the respective vibration elements and output a transmission driving signal to be used for driving the vibration elements; and
a transmission power source that supplies electric power to the transmission circuits,
the ultrasonic diagnostic apparatus further comprising:
a pulse detection unit that detects a transmission signal to be used for generating the transmission driving signal;
an electric power measurement unit that detects an amount of electric power supplied to the transmission circuits as a whole;
a distribution calculation unit that calculates an amount of electric power distributed into each of the vibration elements based on outputs of the pulse detection unit and the electric power measurement unit; and
a power distribution derivation unit that derives electric power having been supplied to each of the plurality of vibration elements based on an output of the distribution calculation unit.

2. The ultrasonic diagnostic apparatus according to claim 1, further comprising:
a transmission pulse generation unit that generates a transmission pulse to be input to each of the plurality of transmission circuits; and
a transmission control unit that generates a control signal to be used for controlling the transmission pulse generation unit based on the power distribution,
wherein the transmission signal is the transmission pulse.

3. The ultrasonic diagnostic apparatus according to claim 1, further comprising:
a transmission pulse generation unit that generates a transmission pulse to be input to each of the plurality of transmission circuits; and a transmission control unit that generates a control signal to be used for controlling the transmission pulse generation unit based on the power distribution, wherein the transmission signal is the control signal.

4. The ultrasonic diagnostic apparatus according to claim 1, wherein the pulse detection unit and the electric power measurement unit perform detection and measurement, respectively, per each ultrasonic beam to be transmitted.

5. The ultrasonic diagnostic apparatus according to claim 1, wherein at least one of the pulse detection unit, the electric power measurement unit and the distribution calculation unit includes a connection selection unit capable of switching processing per mode of each ultrasonic beam to be transmitted.

6. The ultrasonic diagnostic apparatus according to claim 1, wherein the transmission power source is composed of a plurality of power sources, and a plurality of the electric power measurement units are provided in such a manner as to correspond to the plurality of power sources.

* * * * *